US00PP29418P3

(12) United States Plant Patent
Smit

(10) Patent No.: US PP29,418 P3
(45) Date of Patent: Jun. 19, 2018

(54) ***PEPEROMIA* PLANT NAMED 'RANA VERDE'**

(50) Latin Name: *Peperomia albovittata*
Varietal Denomination: Rana Verde

(71) Applicant: Obed Jacob Smit, Sappemeer (NL)

(72) Inventor: Obed Jacob Smit, Sappemeer (NL)

(73) Assignee: Eden Collection B.V., Sappemeer (NL)

( * ) Notice: Subject to any disclaimer, the term of this patent is extended or adjusted under 35 U.S.C. 154(b) by 0 days. days.

(21) Appl. No.: 15/330,449

(22) Filed: Sep. 22, 2016

(65) Prior Publication Data

US 2018/0084699 P1 Mar. 22, 2018

(51) Int. Cl.
*A01H 5/12* (2018.01)

(52) U.S. Cl.
USPC ..... Plt./373
CPC ..... *A01H 5/12* (2013.01)

(58) Field of Classification Search
USPC ..... Plt./373
See application file for complete search history.

(56) References Cited

PUBLICATIONS

UPOV:PLUTO—Plant Variety Database ; citation for Rana Verde Retrieved from the Internet Nov. 6, 2017. ( 1 page total).*

* cited by examiner

*Primary Examiner* — Susan McCormick Ewoldt

(57) ABSTRACT

A new cultivar of *Peperomia* plant named 'Rana Verde' that is characterized by large leaves that are green on the upper surface and yellow-green on the lower surface.

1 Drawing Sheet

Botanical classification: *Peperomia albovittata.*
Variety denomination: 'Rana Verde'.

BACKGROUND OF THE INVENTION

The present invention relates to a new and distinct cultivar of *Peperomia* plant botanically known as *Peperomia albovittata* and hereinafter referred to by the cultivar name 'Rana Verde'.

'Rana Verde' originated from the crossing of the female or seed parent, an unnamed *Peperomia albovittata* cultivar and the male or pollen parent, an unnamed *Peperomia albovittata* cultivar. The crossing was conducted in 2012 in Sappemeer, Netherlands. The resulting seeds were subsequently planted and grown. The cultivar 'Rana Verde' was selected by the inventor in 2013 in a controlled environment as a single plant within the progeny of the stated cross in a cultivated area of Sappemeer, Netherlands.

Asexual reproduction of the new cultivar 'Rana Verde' first occurred by leaf cuttings in 2013 in Sappemeer, Netherlands. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Peperomia* cultivar 'Rana Verde'. These traits in combination distinguish 'Rana Verde' as a new and distinct cultivar apart from other existing varieties of *Peperomia* known by the inventor.

1. *Peperomia* 'Rana Verde' exhibits leaves that are green on the upper surface and yellow-green on the lower surface.
2. *Peperomia* 'Rana Verde' exhibits large leaves.

The closest comparison cultivars are *Peperomia* 'Piccolo Banda' (co-pending U.S. Plant patent application Ser. No. 15/330,398) and *Peperomia* 'Obtipan' (co-pending U.S. Plant patent application Ser. No. 15/330,478). 'Rana Verde' is distinguishable from 'Piccolo Banda' by the following characteristics:

1. *Peperomia* 'Rana Verde' exhibits larger leaves than the leaves of 'Piccolo Banda'.
2. *Peperomia* 'Rana Verde' exhibits leaves that are green on the upper surface. In comparison, the leaves of 'Piccolo Banda' are green with brown veins on the upper surface.

'Rana Verde' is distinguishable from 'Obtipan' by the following characteristics:

1. *Peperomia* 'Rana Verde' exhibits a more compact habit. In comparison, 'Obtipan' has a more upright habit.
2. *Peperomia* 'Rana Verde' exhibits leaves that are green on the upper surface. In comparison, the leaves of 'Obtipan' are darker green in color on the upper surface.
3. *Peperomia* 'Rana Verde' has thinner leaves than the leaves of 'Obtipan'.

'Rana Verde' is distinguishable from the female parent plant, by the following characteristics:

1. The leaves of 'Rana Verde' are green on the upper surface. The leaves of the female parent plant are brown-green on the upper surface.

'Rana Verde' is distinguishable from the male parent plant by the following characteristics:

1. 'Rana Verde' exhibits green leaves on the upper surface. The leaves of the male parent plant are darker green in color on the upper surface.

BRIEF DESCRIPTION OF THE DRAWING

The accompanying photograph illustrates the distinguishing traits of *Peperomia* 'Rana Verde'. The photograph shows an overall view of a 33 week old plant. The photograph was taken using conventional techniques and although colors may appear different from actual colors due to light reflectance, it is as accurate as possible by conventional photographic techniques.

BOTANICAL DESCRIPTION OF THE PLANT

The following is a detailed description of the new *Peperomia* cultivar named 'Rana Verde'. Data was collected in Sappemeer, Netherlands from 33 week old plants grown in a glass greenhouse in 15 cm. diameter containers. The time of year was Winter and the temperature range was 18-25 degrees Centigrade during the day and 15-18 degrees Centigrade at night. The light level was natural light level. No photoperiodic treatments or growth retardants were used. Color determinations are in accordance with The Royal Horticultural Society Colour Chart 2015 edition, except where general color terms of ordinary dictionary significance are used. The growing requirements are similar to the species. 'Rana Verde' has not been tested under all possible conditions and phenotypic differences may be observed with variations in environmental, climatic, and cultural conditions, however, without any variance in genotype.

Botanical classification: *Peperomia albovittata* 'Rana Verde'.
Annual or perennial: Perennial.
Parentage: 'Rana Verde' is a hybrid of the female parent, an unnamed *Peperomia albovittata* cultivar and the male parent an unnamed *Peperomia albovittata* cultivar.
Plant type: Potted plant.
Growth habit: Broad spreading.
Plant shape: Flattened globe shaped.
Suitable container size: 7 cm. pots or larger.
Plant height: 11.3 cm.
Plant width: 21.0 cm.
Vigor: Low to moderate.
Low temperature tolerance: 10° Centigrade.
High temperature tolerance: 35° Centigrade.
Propagation: Leaf cuttings.
Time to initiate roots (summer): 10 days at 18 to 20° C.
Time to initiate roots (winter): 14 days at 18 to 20° C.
Time to produce a rooted cutting (summer): 80 days at 18 to 20° C.
Time to produce a rooted cutting (winter): 100 days at 18 to 20° C.
Growth rate: Low to moderate.
Crop time: Approximately 28 to 33 weeks in Sappemeer, Netherlands.
Root system: Fibrous.
Plant fragrance: None.
Stem:
- *Branching habit.*—Main branches only, no lateral braches.
- *Number of main branches per plant.*—Average 12.
- *Branch dimensions.*—1.9 cm. in length and 0.6 cm. in diameter.
- *Internode length.*—0.125 cm.
- *Stem shape.*—Rounded.
- *Stem texture.*—Smooth.
- *Stem pubescence.*—Absent.
- *Stem angle.*—70 degrees.
- *Stem strength.*—Moderately strong.
- *Stem color* (*young*).—144A.
- *Stem color* (*mature*).—146B with tinges of 152A.
- *Internode color.*—146B with tinges of 152A.

Foliage:
- *Leaf arrangement.*—Alternate.
- *Compound or single.*—Single.
- *Quantity of leaves per branch.*—Average 14.
- *Leaf shape.*—Broad ovate.
- *Leaf aspect.*—Flat to slightly convex.
- *Leaf apex.*—Broad acute.
- *Leaf base.*—Cordate to hastate.
- *Leaf dimensions.*—5.2 cm. in length and 4.9 cm. in width.
- *Texture.*—Glabrous (both surfaces).
- *Leaf luster.*—Upper surface glossy, lower surface matte.
- *Pubescence.*—Absent.
- *Leaf margin.*—Entire.
- *Venation pattern.*—Pinnate, moderately furrowed.
- *Young leaf color* (*upper surface*).—143C.
- *Young leaf color* (*lower surface*).—Between 143C and 144B.
- *Mature leaf color* (*upper surface*).—Between 137A and 147A.
- *Mature leaf color* (*lower surface*).—148C.
- *Vein color* (*upper surface*).—Between 137A and 147A.
- *Vein color* (*lower surface*).—146B to 146C.

Petiole:
- *Petiole dimensions.*—6.6 cm. in length and 0.3 cm. in diameter.
- *Petiole texture.*—Glabrous.
- *Petiole luster.*—Glossy.
- *Petiole pubescence.*—Absent.
- *Petiole strength.*—Moderate.
- *Petiole color.*—178A with fine stripes 147D.

Flower: 'Rana Verde' has not produced flowers to date.
Fruit and seed: 'Rana Verde' has not produced fruit or seed to date.
Disease and pest resistance: Disease and pest resistance has not been observed.

The invention claimed is:

1. A new and distinct variety of *Peperomia* plant named 'Rana Verde' as described and illustrated.

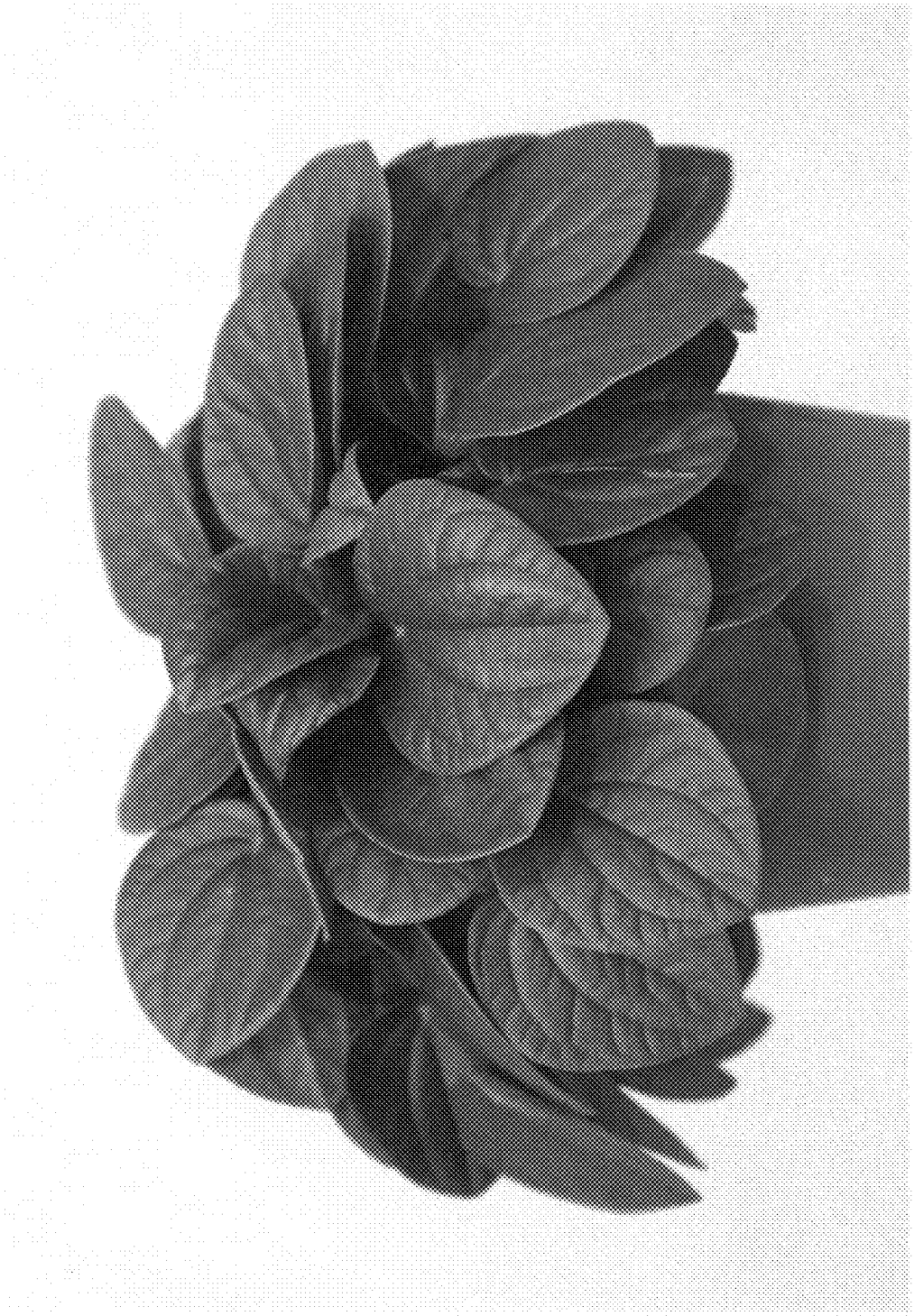

* * * * *